(12) United States Patent
Fromreide et al.

(10) Patent No.: US 7,824,475 B2
(45) Date of Patent: Nov. 2, 2010

(54) AIR CLEANING DEVICE

(76) Inventors: Hans-Jacob Fromreide, Elisenbergveien 5, Oslo (NO) N-0265; Tomm Slater, Morells vei 1 c, Oslo (NO) N-0487

( * ) Notice: Subject to any disclaimer, the term of this patent is extended or adjusted under 35 U.S.C. 154(b) by 1130 days.

(21) Appl. No.: 10/564,035

(22) PCT Filed: Jun. 27, 2002

(86) PCT No.: PCT/NO02/00236
§ 371 (c)(1), (2), (4) Date: Feb. 23, 2005

(87) PCT Pub. No.: WO03/002261
PCT Pub. Date: Jan. 9, 2003

(65) Prior Publication Data
US 2009/0173230 A1    Jul. 9, 2009

(30) Foreign Application Priority Data
Jun. 28, 2001    (NO) ................... 20013250

(51) Int. Cl.
*B03C 3/014* (2006.01)
(52) U.S. Cl. ............. 96/44; 95/66; 95/67; 95/73; 95/75; 96/49; 96/50; 96/53; 96/63
(58) Field of Classification Search ............ 96/44–47, 96/49, 50, 53, 63, 64; 95/66–68, 71–73, 95/75, 78; 55/282.3, DIG. 10, DIG. 38
See application file for complete search history.

(56) References Cited

U.S. PATENT DOCUMENTS

| | | | | |
|---|---|---|---|---|
| 2,001,700 A | | 5/1935 | Barthel | |
| 2,207,576 A | * | 7/1940 | Brown | 95/71 |
| 2,583,898 A | * | 1/1952 | Smith | 204/168 |
| 2,825,102 A | * | 3/1958 | Hicks et al. | 422/4 |
| 3,054,243 A | * | 9/1962 | Bowie | 95/73 |
| 3,124,437 A | * | 3/1964 | Lagarias | 95/75 |
| 3,958,959 A | * | 5/1976 | Cohen et al. | 95/64 |
| 4,202,674 A | | 5/1980 | Rodenberger | |
| 4,204,844 A | * | 5/1980 | Pilat | 95/2 |
| 4,225,323 A | * | 9/1980 | Zarchy et al. | 95/73 |
| 4,289,504 A | * | 9/1981 | Scholes | 95/73 |
| 4,305,909 A | * | 12/1981 | Willett et al. | 422/169 |
| 4,624,763 A | * | 11/1986 | Chimenti | 204/562 |

(Continued)

FOREIGN PATENT DOCUMENTS

CA    2 338 642    2/2000

(Continued)

*Primary Examiner*—Richard L Chiesa
(74) *Attorney, Agent, or Firm*—Christian D. Abel

(57) ABSTRACT

According to one aspect of the invention a device for purification of air is provided, including
- a metal plate
- electrical connections connected to the metal plate in order to impress a voltage on the metal plate,
- a heating element for heating the metal plate, and
- a nozzle connected to a water supply in order to spray the metal plate with water.

In further embodiments the device includes a metallic cylinder, a fan disposed at one end of the cylinder and a restriction disposed at the other end of the cylinder, together with live coils for providing an electric field, where the centre of the electric field around the coils coincides with the location of the device's other units.

8 Claims, 3 Drawing Sheets

U.S. PATENT DOCUMENTS

| | | | |
|---|---|---|---|
| 5,364,457 A * | 11/1994 | Cameron | 96/27 |
| 5,595,587 A | 1/1997 | Steed | |
| 5,626,652 A * | 5/1997 | Kohl et al. | 96/45 |
| 6,126,722 A * | 10/2000 | Mitchell et al. | 95/57 |
| 6,129,781 A * | 10/2000 | Okamoto et al. | 96/25 |
| 6,251,170 B1 | 6/2001 | Hironaka | |
| 6,302,945 B1 * | 10/2001 | Altman et al. | 96/44 |
| 7,427,313 B2 * | 9/2008 | Fromreide et al. | 96/27 |
| 2009/0173230 A1 * | 7/2009 | Fromreide et al. | 96/44 |

FOREIGN PATENT DOCUMENTS

| | | |
|---|---|---|
| EP | 0 424 335 | 4/1991 |
| EP | 424 335 | 4/1991 |
| HU | 211359 | 8/1990 |
| JP | 63-196417 | 12/1988 |
| JP | 2-17248 | 2/1990 |
| JP | 3-11935 | 1/1991 |
| JP | 6-47310 A * | 2/1994 |
| JP | 10-170071 | 6/1998 |
| JP | 10-244183 | 9/1998 |
| JP | 2000-093837 | 4/2000 |
| JP | 20035 4787 | 12/2000 |
| JP | 2001-46909 | 2/2001 |

* cited by examiner

AIR CLEANING DEVICE

This application is a National Stage application under 35 U.S.C. §371 of PCT/NO2002/000236, filed Jun. 27, 2002.

The invention relates to a device for purification of air, especially for purification of indoor air.

Many indoor environments have serious problems with air quality. Odour and dust and too much or too little humidity result in discomfort and may lead to health problems.

There are several methods of purifying the indoor air, the most common being mechanical filtration of circulating air and ionisation of molecules, which are attracted into a voltage field.

EP 424 335 relates to a procedure and an apparatus for the purification of air, flue gases and the like, where the purification is performed in a shaft, duct or a pipe containing electrodes. There is a potential difference between the electrodes and the wall(s) in the shaft/duct/pipe. The electrodes ionise impurity particles in the air/flue gases and these are then attracted to the walls to which they become attached. The walls are cleaned of impurities by flushing them with water at regular intervals.

The disadvantage of devices of this type is that they employ high voltage in order to ionise particles or molecules, thereby involving a high voltage source in the device, which may represent a potential risk in case of contact.

The object of the invention is to provide a device for purification of indoor air which works effectively on several types of impurities and which does not involve any risk.

The object of the invention is achieved by means of the features in the patent claims.

The device according to the invention comprises a metal plate, preferably of beryllium bronze. The metal plate has two functions. Firstly, it is electrically connected to a voltage source, thus forming a potential difference between the metal plate and the housing of the device (the chassis). The potential difference attracts electrically charged impurity particles in the air.

Secondly, the metal plate is heated to a specific temperature, preferably 500° C., thus causing the attracted impurities that strike the metal plate to be burned on to it. Since the metal plate gradually becomes contaminated, it can be sprayed with water at regular intervals in order to loosen the impurities and hosed down in a bath, which can subsequently be emptied into the building's drainage system. In this manner the impurities are removed from the air quickly and efficiently.

In a preferred embodiment the device is equipped with a metallic cylinder and a fan disposed at one end of the cylinder, which blows air into the cylinder, thus producing an overpressure in the cylinder. The other end of the cylinder has a restriction through which air passes. Impurities will become attached to the cylinder.

In another preferred embodiment of the invention, the device is surrounded by current conducting coils. The coils are wound in such a manner that the electric fields generated round these coils form a common electric field. The device's other units are placed in the centre of this field.

The invention will now be described in greater detail by means of an example, with reference to the accompanying drawings, in which.

Figure 1:
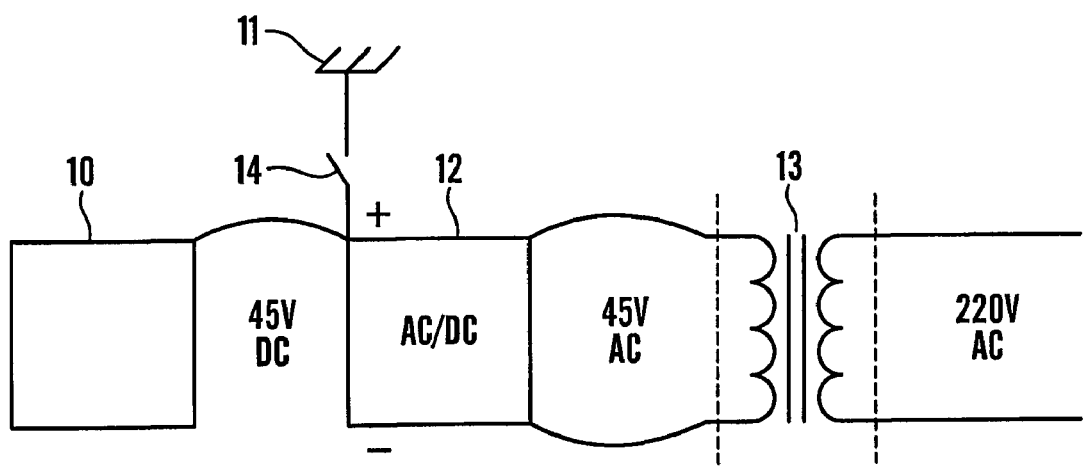
FIG. 1 illustrates the electrical connections for a metal plate in the device according to the invention.
Figure 2:
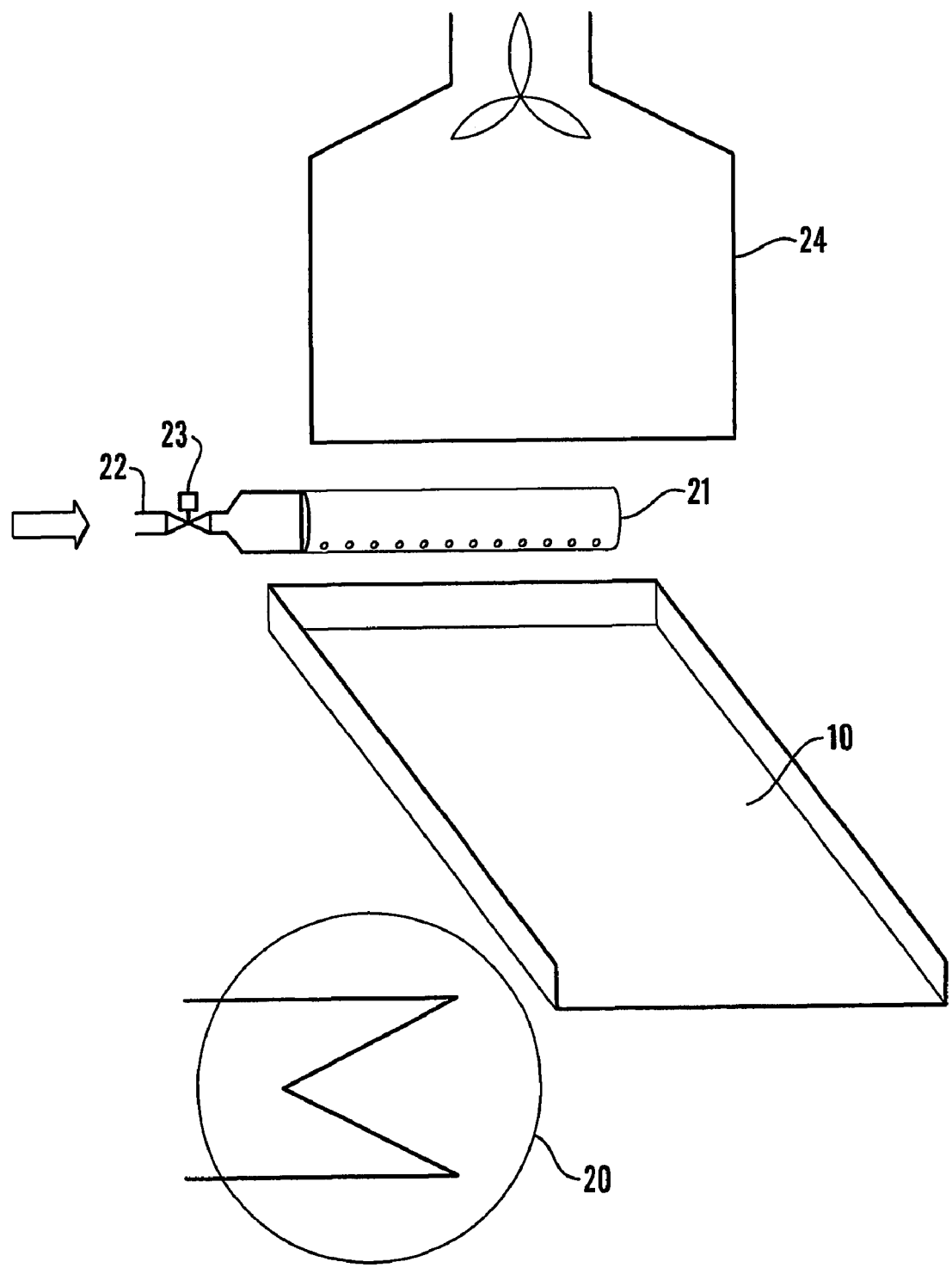
FIG. 2 illustrates the metal plate with nozzle, heating element and ventilation means.

In a preferred embodiment the device according to the invention comprises a metal plate in a configuration as illustrated in FIGS. 1 and 2.

FIG. 1 illustrates how a metal plate 10 is electrically insulated from the environment, but electrically connected to a rectifying bridge 12. The rectifying bridge 12 is electrically connected to a transformer 13 for transforming down an alternating voltage of 220V from the ordinary power supply to an alternating voltage of 45V. The output on the rectifying bridge supplies a direct voltage of 45V. The rectifying bridge and the metal plate are earthed via a switch 14 (to the chassis). With this configuration the potential difference between the metal plate and earth 11 can be altered by connecting and disconnecting the switch. The connection and disconnection of the switch may be controlled by a computer, and will preferably be carried out in such a manner that the metal plate alternates between neutral and positive potential difference relative to earth.

FIG. 2 illustrates the metal plate 10, which can be heated by means of a heating element 20 that preferably produces an output of 700 W. The metal plate is preferably tilted.

Particles that strike the metal plate 10 will become attached thereto and burned on to it. The metal plate is preferably made of beryllium bronze, which is an alloy with small amounts of beryllium (2-7%) in copper, which gives extremely hard and solid alloys. They are the strongest copper alloys that exist and the best electrical conductors of all high-strength alloys. Alternatively, the metal plate may be made of pure copper or another suitable metal/metal alloy.

A nozzle 21 is located at the upper end of the metal plate 10. The nozzle is supplied with water from the ordinary water mains via water pipes 22 through a valve 23. When the water from the nozzle 21 strikes the metal plate 10, it evaporates and this vapour is sucked up in a suction unit 24 and drained off. The suction unit 24 may be covered in a thermally insulating material to prevent the metal plate from becoming cooled. In order to clean the metal plate 10 of impurities, the nozzle 21 sprays water on to the metal plate 10 at regular intervals. The intervals depend on the degree of contamination and the type of metal, but is normally 3-5 times per 24 hour period for beryllium bronze and 5-10 times per 24 hour period for copper.

Figure 3:
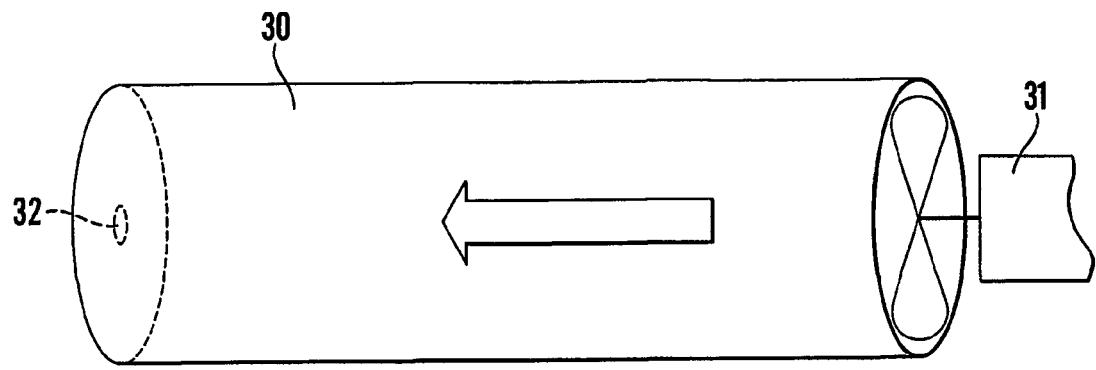
FIG. 3 illustrates a metallic cylinder with a fan that creates overpressure in the cylinder.

In an alternative embodiment in FIG. 3, the metal plate 10 is combined with a metallic cylinder 30, which has a fan 31 at one end and a restriction 32, which restricts the airflow, at the other end. The cylinder will attract molecules, thereby increasing the efficiency of the device according to the invention.

Figure 4:
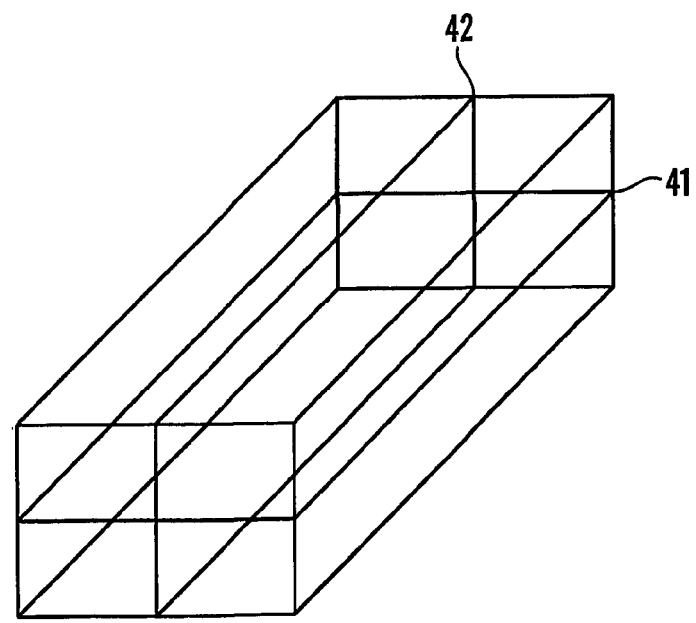
FIG. 4 illustrates a preferred orientation of current conducting coils.

In addition, the device according to the invention may comprise coils 41 and 42 as illustrated in FIG. 4, wound by electrical conductors and connected in series with the heating element 20 in FIG. 2. The electric fields generated around the coils create a total electric field. The coils are preferably wound around the device in such a manner that the location of the centre in this total electric field coincides with the location of the device's other units.

In yet another alternative embodiment the device may comprise an air humidifier for increasing the humidity of the air surrounding the device.

The invention claimed is:
1. A device for purification of air comprising
a metal plate
electrical connections connected to the metal plate in order to impress a voltage on the metal plate, the device further comprising
- a heating element for heating the metal plate,
- a nozzle connected to a water supply in order to spray the metal plate with water, and
- current conducting coils in order to provide an electromagnetic field, where the centre of the electromagnetic field around the coils coincides with the location of the device's other units.

2. A device as in claim 1,
wherein the heating element is comprised of an electrical resistor and produces an output of 700W.

3. A device as in claim 1,
wherein the metal plate reaches a temperature of approximately 500° C.

4. A device as in claim 1,
further comprising a metallic cylinder, a fan disposed at one end of the cylinder and a restriction disposed at the other end of the cylinder.

5. A device as in claim 1,
wherein the coils are electrically connected in series to the heating element.

6. A device as in claim 1 wherein the metal plate is made of beryllium bronze.

7. A device as in claim 1 wherein the metal plate is made of copper (Cu).

8. A device as in claim 1 further comprising a suction unit for removing the vapour produced when the water from the nozzle strikes the hot metal plate.

* * * * *